(12) United States Patent
Ahn

(10) Patent No.: US 8,708,901 B2
(45) Date of Patent: Apr. 29, 2014

(54) HEALTH MONITORING SYSTEM WITH A WAVEGUIDE TO GUIDE A WAVE FROM A POWER SOURCE

(75) Inventor: Doyeol Ahn, Seoul (KR)

(73) Assignee: University of Seoul Industry Cooperation Foundation, Seoul (KR)

(*) Notice: Subject to any disclaimer, the term of this patent is extended or adjusted under 35 U.S.C. 154(b) by 1053 days.

(21) Appl. No.: 12/650,031

(22) Filed: Dec. 30, 2009

(65) Prior Publication Data

US 2011/0160542 A1 Jun. 30, 2011

(51) Int. Cl.
*A61B 5/00* (2006.01)
*H01P 3/12* (2006.01)
*H02J 7/02* (2006.01)
*H02J 5/00* (2006.01)
*H01Q 1/24* (2006.01)
*H01Q 9/06* (2006.01)
*H01Q 1/27* (2006.01)
*H01Q 1/32* (2006.01)
*H01Q 23/00* (2006.01)
*H01P 3/00* (2006.01)
*H01P 3/16* (2006.01)
*H02J 7/00* (2006.01)
*H01Q 1/00* (2006.01)
*H01Q 15/00* (2006.01)

(52) U.S. Cl.
CPC .......... *H02J 7/025* (2013.01); *H02J 5/005* (2013.01); *H01Q 1/248* (2013.01); *H01Q 15/00* (2013.01); *H01Q 9/065* (2013.01); *H01Q 1/273* (2013.01); *H01Q 1/3233* (2013.01); *H01Q 23/00* (2013.01); *H01P 3/00* (2013.01); *H01P 3/16* (2013.01)

USPC .......... 600/300; 600/301; 359/332; 385/122; 340/539.22; 340/539.12; 340/539.26; 343/793; 343/700 MS; 343/911 R; 343/907; 333/239

(58) Field of Classification Search
None
See application file for complete search history.

(56) References Cited

U.S. PATENT DOCUMENTS

| 5,068,669 | A | * | 11/1991 | Koert et al. | 343/700 MS |
|---|---|---|---|---|---|
| 5,218,374 | A | * | 6/1993 | Koert et al. | 343/789 |
| 6,682,480 | B1 | * | 1/2004 | Habib et al. | 600/300 |
| 7,486,236 | B2 | * | 2/2009 | Sarehraz et al. | 343/700 MS |
| 7,888,586 | B2 | * | 2/2011 | Yamamoto et al. | 136/244 |
| 8,115,683 | B1 | * | 2/2012 | Stefanakos et al. | 343/700 MS |
| 2007/0109023 | A1 | | 5/2007 | Beausoliel | |
| 2007/0196065 | A1 | | 8/2007 | Lee et al. | |
| 2007/0263278 | A1 | | 11/2007 | Chowdhury et al. | |
| 2008/0001735 | A1 | * | 1/2008 | Tran | 340/539.22 |
| 2009/0033586 | A1 | * | 2/2009 | Sanada | 343/911 R |
| 2009/0237093 | A1 | * | 9/2009 | Kim et al. | 324/637 |
| 2010/0309078 | A1 | * | 12/2010 | Rofougaran et al. | 343/776 |
| 2011/0232211 | A1 | * | 9/2011 | Farahi | 52/173.3 |

OTHER PUBLICATIONS

Ali, M. et al; "A New Circularly Polarized Rectenna for Wireless Power Transmission and Data Communication"; IEEE Antennas and Wireless Propagation Letter, vol. 4, 2005; p. 205-208.*

(Continued)

*Primary Examiner* — Bill Thomson
*Assistant Examiner* — Marie Archer
(74) *Attorney, Agent, or Firm* — Dorsey & Whitney LLP

(57) ABSTRACT

A health monitoring system includes a waveguide that receives a wave transmitted from an external power source and that guides the wave to reach within a width of a rectenna. The waveguide may include a negative refractive index medium and/or a surface plasmon medium.

22 Claims, 13 Drawing Sheets

(56) References Cited

OTHER PUBLICATIONS

Heikkinen, J.; "A Novel Dual-Frequency Circularly Polarized Rectenna"; IEEE Antennas and Wireless Propagation Letter, vol. 2, 2003; p. 330-333.*

Mateu, M; "Energy Harvesting from Passive Human Power", PhD Thesis Project Electronic Engineering, Jan. 2004; p. 1-40.*

McSpadden, J. O; "Design and Experiments of a High-Conversion-Efficiency 5.8 GHz Rectenna"; IEEE Transactions on Microwave Theory and Techniques, vol. 46, No. 12, Dec. 1998; p. 2053-2060.*

Sarehraz, M. et al; "Rectenna development for solar energy collection"; IEEE, 2005, p. 78-81.*

Shalev. V. et al; "Negative index of refraction in optical metamaterials"; Optics Letters, vol. 30, No. 24, Dec. 15, 2005; p. 3356-3358.*

Yoo, T. et al; "35 GH Rectenna Implemented with a patch and a microstrip dipole antenna"; IEE MTT-S Digest, 1992, p. 345-348.*

Yang, G. et al; "A Multi-Functional Stacked Patch Antenna for Wireless Power Beaming and Data Telemetry"; IEEE 2005, p. 359-362.*

Sudou, M. et al; "A novel RF induced power supply system for monolithically integrated ubiquitous micro sensor nodes"; Sensors and Actuators A 145-146 (2008) 343-348.*

Acuna, G. et al; "Surface plasmons in terahertz metamaterials"; Optics Express vol. 16, No. 23; Nov. 10, 2008; p. 18745-18751.*

R. A. Shelby, et al., "Experimental Verification of a Negative Index of Refraction", Apr. 6, 2001, p. 77, Science, vol. 292, American Association for the Advancement of Science.

D. R. Smith, et al., "Metamaterials and Negative Refractive Index", Aug. 6, 2004, p. 788, Science, vol. 305, American Association for the Advancement of Science.

D. R. Smith et al., "Loop-wire medium for investigating plasmons at microwave frequencies", Sep. 6, 1999, p. 1425, Applied Physics Letters, vol. 75 No. 10, American Institute of Physics.

J. B. Pendry, "Negative Refraction Makes a Perfect Lens", Oct. 30, 2000, p. 3966, Physical Review Letters, vol. 85 No. 18, American Physical Society.

D. R. Smith et al., "Composite Medium with Simultaneously Negative Permeability and Permittivity", p. 4184, Physical Review Letters, vol. 84 No. 18, American Physical Society.

Ulf Leonhardt et al., "General relativity in electrical engineering", p. 1, New Journal of Physics, vol. 8, No. 247, Institute of Physics.

Richard W. Ziolkowski, et al "Matamaterial-Based Efficient Electrically Small Antennas" IEEE Transactions on Antennas and Propagation, vol. 54, No. 7, pp. 2113-2130, Jul. 2006.

A. A. Basharin, et al "The Radiation of Antennas Based on Metamaterial Waveguides" 3rd International Congress on Advanced Electromagnetic Materials in Microwaves and Optics, London, Aug. 30-Sep. 4, 2009, pp. 224-226.

Kunio Sakakibara, et al "Waveguide Antenna Applications of Metamaterials to Leaky-Wave Slotted Waveguide Array" Proceedings of iWAT, 2008, Chiba, Japan, pp. 63-66.

Australian Patent Office; International Search Report and Written Opinion in corresponding PCT application (PCT/KR2010/009306) mailed Mar. 2, 2011.

Barnes, W.L. et al., "Surface Plasmon Subwavelength Optics," Nature, vol. 424, Aug. 14, 2003, pp. 824-830.

\* cited by examiner

HEALTH MONITORING SYSTEM WITH A WAVEGUIDE TO GUIDE A WAVE FROM A POWER SOURCE

BACKGROUND

A passive device does not require a source of energy for its operation. Examples of passive devices are electrical resistors, electrical capacitors, diodes, optical fibers, cables, wires and filters. When a passive device wirelessly operates, it can operate with an external power source, such as an electric power carried on a wave. An operation of such passive device may depend on a degree of a power coupling between the passive device and the external power source.

DETAILED DESCRIPTION

Figure 1A:
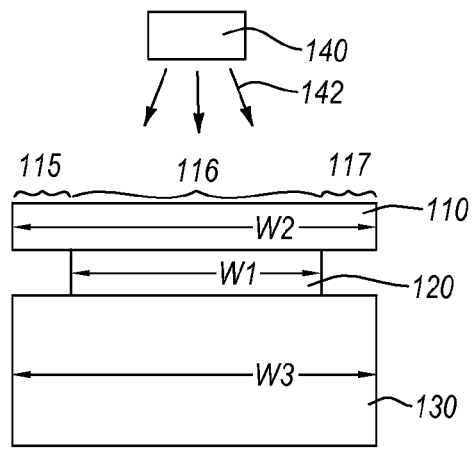
FIG. 1(a) is a schematic diagram of an illustrative embodiment of an apparatus including a waveguide operable with a rectenna.

In one embodiment, an apparatus includes a waveguide configured to receive a wave transmitted from an external power source and to guide the wave to reach within a width of a rectenna.

The waveguide may include a negative refractive index medium to refract the wave to reach within the width of the rectenna. The negative refractive index medium may include a metamaterial. The metamaterial may include a two-dimensional array of repeated unit cells of copper strips and split ring resonators on interlocking strips of standard circuit board material. The metamaterial may include a quantum metamaterial. The quantum metamaterial may have a manipulated chemical composition and/or a structure of a material.

The waveguide may include a surface plasmon medium to generate a surface plasmon resonance. The surface plasmon medium may include two or more components and one or more dielectric components interposed between the two or more components. Each of the two or more components may be composed of a surface plasmon material and each of the one or more dielectric components may be composed of a dielectric material. A permittivity of the two or more components may be greater than a permittivity of the one or more dielectric components. The surface plasmon material may include Au, Ag, Cu, Ti, Cr or an alloy thereof. The dielectric material may include air or silicon dioxide. The surface plasmon medium may include a loop-wire structure. The loop-wire structure may include a plurality of wire elements. Each wire element may include at least one vertical wire with at least one planar loop wound at intervals.

The surface plasmon medium may include at least two components being spaced from one another. Each component is composed of a surface plasmon material. The rectenna may include a rectifier part positioned under the waveguide and at least one antenna part protruding from a part of the rectifier part such that the antenna part is located between the at least two components. The at least one antenna part may be composed of a dielectric material.

The waveguide may include both the negative refractive index medium and the surface plasmon medium.

The rectenna may be positioned under the waveguide. The width of the rectenna may be smaller than a width of the waveguide. The width of the rectenna may be about 0.5 nm to 300 mm.

In another embodiment, a health monitoring system includes a detection device, a waveguide, a rectenna and a transmitter. The detection device may be configured to detect a health status of a creature. The waveguide may be configured to receive a wave transmitted from an external power source and to guide the wave to reach within a width of a rectenna. The rectenna may be positioned under the waveguide, and configured to receive and to rectify the guided wave to generate an electric power to drive the detection device. The transmitter may be configured to transmit the detected health status to an external device.

The detection device may comprise at least one of a chemosensor and a biosensor to sense the health status. The health monitoring system may be inserted into a body of the creature or attached on an outer surface of the creature. The external device may include a monitor to display the detected health status.

In still another embodiment, a method includes receiving a wave from an external power source, and guiding the received wave to reach within a width of a rectenna. The method may further include receiving, at the antenna, the guided wave, rectifying, at the rectenna, the wave to generate a DC electricity, and supplying the generated DC electricity to an electric device. The received wave may be guided within a width of a rectenna by at least one of using negative refraction and using a surface plasmon resonance.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 1B:
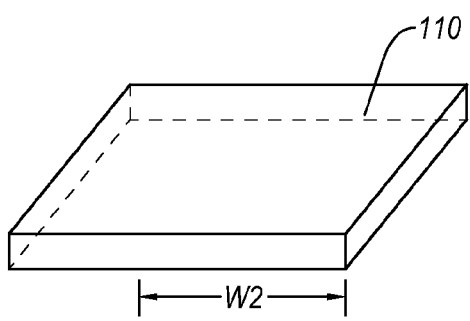
FIG. 1(b) illustrates the rectenna of FIG. 1(a) with a hexahedron shape.
Figure 1B:
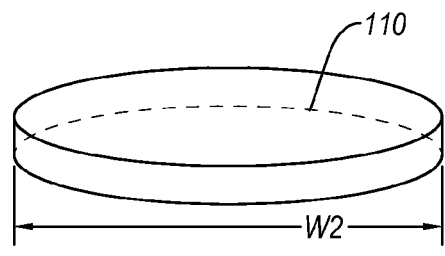
Figure 1B:
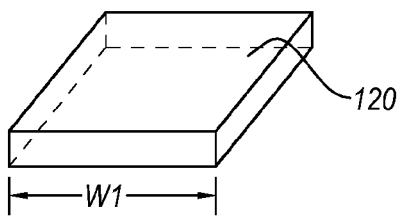
Figure 1C:
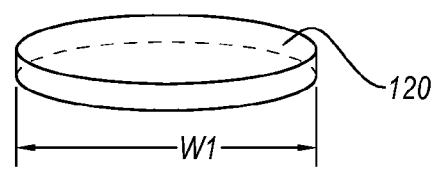
FIG. 1(c) illustrates the rectenna of FIG. 1(a) with a disk shape.

FIG. 1(a)-1(c) is a schematic diagram of an illustrative embodiment of an apparatus including a waveguide operable with a rectenna. FIG. 1(a) illustrates an apparatus including a waveguide 110. Waveguide 110 may include a negative refractive index medium. As used herein, the term "the negative refractive index medium" refers to a medium that has a negative refractive index. When a permeability and permittivity of a medium are simultaneously negative, the medium may have a negative refractive index. The negative refractive medium may be configured with a particular physical structure or a particular chemical composition or structure. More details on the physical structure and the chemical composition or structure will be described later. FIG. 1(a) further illustrates a rectenna 120 to generate a power for an electric device 130 in response to a wave 142 transmitted from waveguide 110, electric device 130 to receive the power from rectenna 120, and an external power source 140 to transmit wave 142 toward waveguide 110. The rectenna 120 has a width W1, the waveguide 110 has a width W2, and the electric device 130 has a width W3 as illustrated in FIG. 1A.

As used herein, electric device 130 is a passive device which operates with an electric power provided by external power source 140. For example, electric device 130 may be a sensor that detects a signal in response to an electric power provided by external power source 140. For another example, electric device 130 may be a signal transmitter that emits an electric signal in response to the electric power provided by external power source 140. Electric device 130 may have dimensions of several nanometers to several micrometers. As used herein, the term "dimensions" of electric device 130 may refer to a width and/or a thickness of electric device 130. By way of examples, electric device 130 may have a width of about 1 nm to 500 mm, about 3 nm to 100 mm or about 20 nm to 1 mm, and a thickness of about 0.5 nm to 300 mm, about 1 nm to 50 nm or about 10 nm to 30 nm, without limitation.

External power source 140 transmits wave 142 carrying an electric power. As used herein, the term "wave" may refer to an oscillation that propagates through space and time with transference of energy. For example, wave 142 may include an electromagnetic wave, such as, a radio wave, a microwave, an infrared radiation, an ultraviolet radiation, a visible light, an X-ray and a gamma ray, without limitation. External power source 140 may be any known type of power transmitter that can transmit the electric power over wave 142. For example, external power source 140 may be an AC power source which is connected to a commercial power, such as 110V and 220V, and transmits a wave carrying AC power over the air. Although FIG. 1(a) illustrates that external power source 140 transmits more than one wave 142 for the purpose of description, external power source 140 may transmit one wave 142.

Rectenna 120 refers to a rectifying antenna. Rectenna 120 converts an electric power into a DC electricity by receiving a wave carrying an electric power and rectifying the wave. In one embodiment, rectenna 120 may include one or more conducting elements and diodes. Wave 142 creates an alternating current in the conducting elements and then the alternating current is rectified by the diodes to generate a DC current. This generated DC current is provided to electric device 130 as an electric power to drive electric device 130. Rectenna 120 may be in the form of any well-known rectenna constitution. By way of examples, rectenna 120 may include a multiple number of phased antenna elements including conducting elements and Schottky diodes placed between the antenna elements, but the constitution of rectenna 120 is not limited thereto.

Rectenna 120 may have various shapes, for example, a hexahedron, a cube or a disk, without limitation. FIG. 1(b) illustrates the rectenna the with a hexahedron shape and FIG. 1(c) illustrates the rectenna 120 with a disk shape. FIGS. 1(b) and 1(c) also illustrate the width W1 of the rectenna 120 for, respectively, the hexahedron shape and the disk shape. Rectenna 120 may have dimensions of several nanometers to several micrometers. As used herein, the dimension of rectenna 120 may refer to a width or a thickness when rectenna 120 has a hexahedron or cube shape, or a diameter or a thickness when rectenna 120 has a disk shape. Although FIG. 1(a) illustrates rectenna 120 having the hexahedron shape for the simplicity of description, it is apparent to those skilled in the art that rectenna 120 can have any other shape and the dimension can refer to the diameter or the thickness. By way of examples, rectenna 120 may have a width of about 0.5 nm to 300 mm, about 1 nm to 100 mm or about 20 nm to 1 mm, and a thickness of about 0.1 nm to 100 mm, about 1 nm to 50 mm or about 20 nm to 500 nm, without limitation. In one embodiment, the width of rectenna 120 may be smaller than the width of electric device 130 by several nanometers to several micrometers (for example, about 0.5 nm to 300 nm, about 1 nm to 100 nm or about 30 nm to 50 nm, without limitation).

Figure 4A:
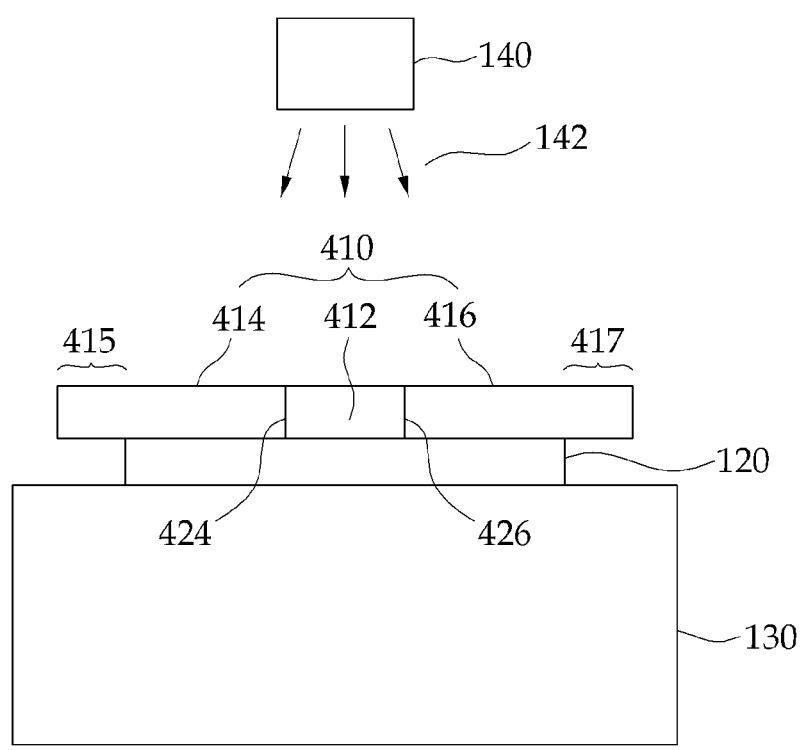
FIG. 4(a) is a schematic diagram of another illustrative embodiment of an apparatus including a waveguide operable with a rectenna.
Figure 6:
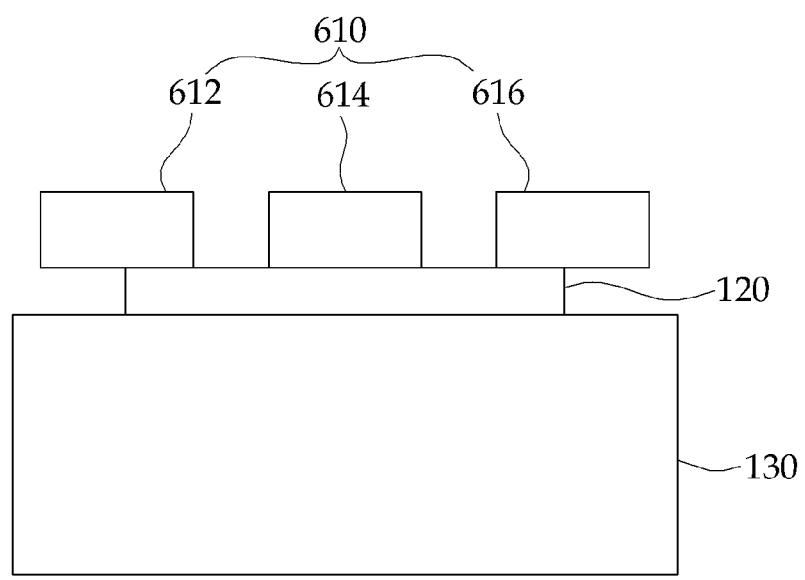
FIG. 6 is a schematic diagram of still another embodiment of an apparatus including a waveguide operable with a rectenna.
Figure 7:
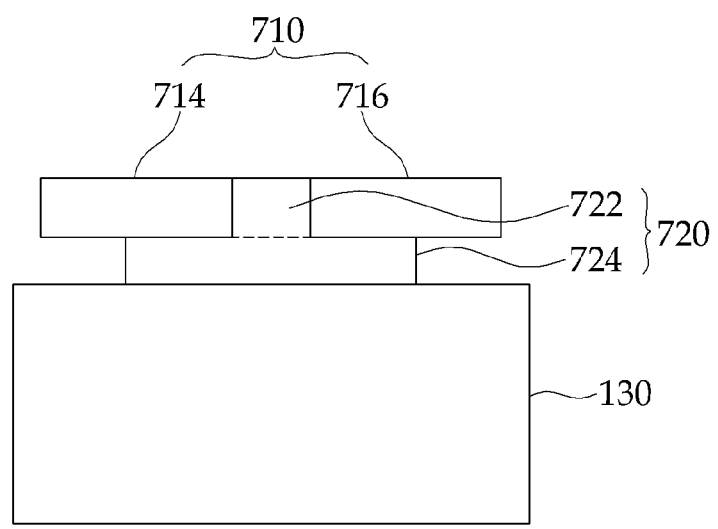
FIG. 7 is a schematic diagram of still another embodiment of an apparatus including a waveguide operable with a rectenna.

Waveguide 110 is configured to receive wave 142 transmitted from external power source 140 and to guide wave 142 to desired directions, for example, within a width of rectenna 120. In some embodiments, waveguide 110 may have various shapes, for example, a hexahedron, a cube or a disk, without limitation. By way of examples, waveguide 110 may have a width or a diameter of about 1 nm to 400 mm, about 3 nm to 50 mm or about 10 nm to 500 nm, and a thickness of about 0.1 nm to 100 mm, about 1 nm to 50 mm or about 20 nm to 500 nm, without limitation. Waveguide 110 may have a left end portion 115, a central portion 116 and a right end portion 117. Central portion 116 is placed on rectenna 120 and has the same width as that of rectenna 120. Left and right end portions 115 and 117 are respectively placed on the left and right sides of central portion 116. By way of examples, each of left and right end portions 115 and 117 may have a width of about 0.25 nm to 50 mm, about 1 nm to 25 mm or about 5 nm to 250 nm, without limitation. In other embodiments, a waveguide may include more than one component. For example, the waveguide may have two components as depicted in FIG. 7 or three components as depicted in FIGS. 4(a) and 6, which will be described later.

As described above, waveguide 110 may include a negative refractive index medium. Detailed description with regard to the negative refractive index medium and how waveguide 110 guides a wave will be described with reference to FIGS. 2(a) through 2(c).

Figure 2A:
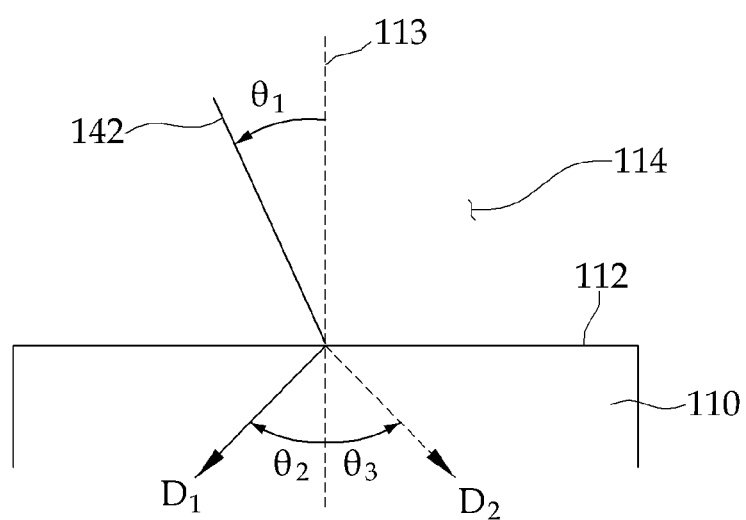
FIG. 2(a) is a schematic diagram illustrating a wave path at an interface between a normal medium and a waveguide having a negative refractive index medium.

FIG. 2(a) is a schematic diagram illustrating a wave path at an interface between a normal medium 114 and waveguide 110. Here, normal medium 114 refers to a medium that has a positive refractive index, such as an air or silicon dioxide.

FIG. 2(a) illustrates that wave 142 propagates from an external power source (not shown) toward waveguide 110 with an angle $\theta_1$ in normal medium 114 with respect to a vertical line 113. Vertical line 113 is perpendicular to an interface 112 between normal medium 114 and waveguide 110. FIG. 2(a) further illustrates that wave 142 refracts toward a direction $D_1$, rather than a direction $D_2$, when it arrives at interface 112. Direction $D_1$ is inclined with an angle $\theta_2$ in waveguide 110 with respect to vertical line 113. Direction $D_2$ is inclined with an angle of $\theta_3$ with respect to vertical line 113.

The refraction of wave 142 toward direction $D_1$ can be explained by applying the Snell's law. The Snell's law is represented by Equation (1) below.

$$n_1 \sin \theta_1 = n_2 \sin \theta_2 \qquad \text{Equation (1)}$$

Here, a variable $n_1$ and a variable $n_2$ denote refractive index of normal medium 114 and waveguide 110, respectively. According to Equation (1), angles $\theta_1$ and $\theta_2$ have opposite signs because variable $n_1$ is positive and variable $n_2$ is negative. Since angle $\theta_1$ has a positive sign in FIG. 2(a), angle $\theta_2$ has a negative sign to satisfy the Snell's law. As used herein, the positive sign of angle $\theta_1$ indicates that angle $\theta_1$ is measured in the counterclockwise direction at vertical line 113, and the negative sign of angle $\theta_2$ refers that angle $\theta_2$ is measured in the clockwise direction at vertical line 113. Thus, wave 142 refracts toward direction $D_1$ having a negative sign of angle $\theta_2$, instead of refracting toward direction $D_2$ having a positive sign of angle $\theta_3$ with regard to vertical line 113.

Figure 2B:
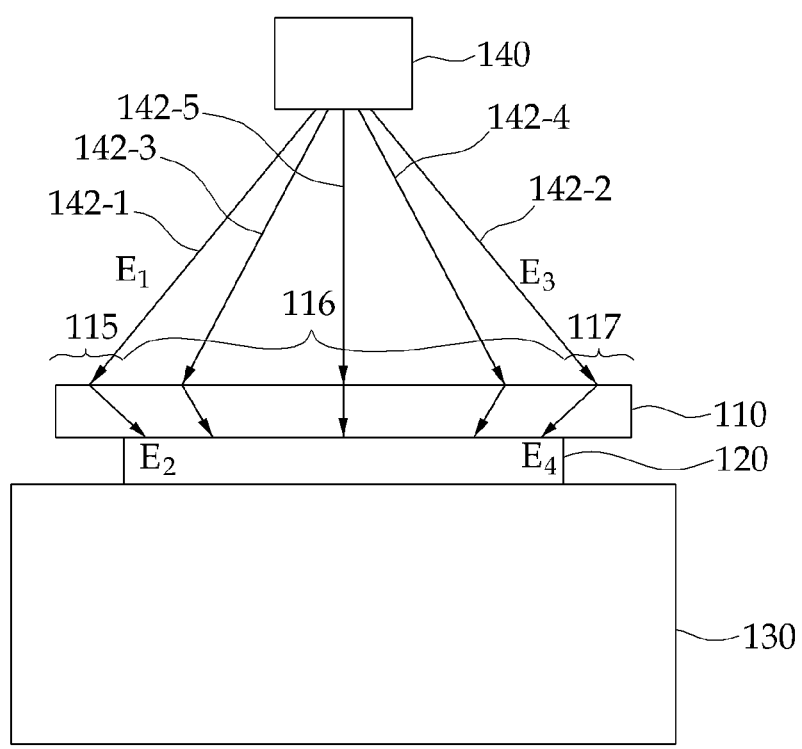
FIG. 2(b) is a schematic diagram for illustrating how waves are guided by a waveguide within a width of a rectenna.

FIG. 2(b) is a schematic diagram for illustrating how waveguide 110 guides waves to refract within the width of rectenna 120. External power source 140 transmits waves, for example, waves 142-1 to 142-5, carrying an electric power to drive electric device 130. For the simplicity of description, FIG. 2(b) illustrates that five waves 142-1 to 142-5 are transmitted from external power source 140 to rectenna 120, but it will be apparent to one of ordinary skill in the art that external power source 140 may transmit less or more than five waves. Wave 142-1 is transmitted from external power source 140 to left end portion 115 of waveguide 110 in a direction $E_1$. When wave 142-1 arrives at left end portion 115 of waveguide 110, it refracts toward a direction $E_2$ due to the negative refractive index of waveguide 110. Because it is refracted toward direction $E_2$, wave 142-1 reaches rectenna 120, although it has reached left end portion 115 which is outside the width of rectenna 120. Likewise, wave 142-2 is transmitted from external power source 140 to right end portion 117 in a direction $E_3$. When wave 142-2 arrives at right end portion 117 which is outside the width of rectenna 120, it refracts toward a direction $E_4$ and reaches rectenna 120. Waves 142-3 and 142-4 arrive at central portion 116 of waveguide 110 which corresponds to rectenna 120. As shown in FIG. 2(b), waves 142-3 and 142-4 are also refracted at central portion 116 toward rectenna 120, and then, reaches rectenna 120. Wave 142-5 also arrives at rectenna 120 through central portion 116. But, wave 142-5 does not refract at central portion 116 because wave 142-5 exactly vertically arrives at central portion 116.

Figure 2C:
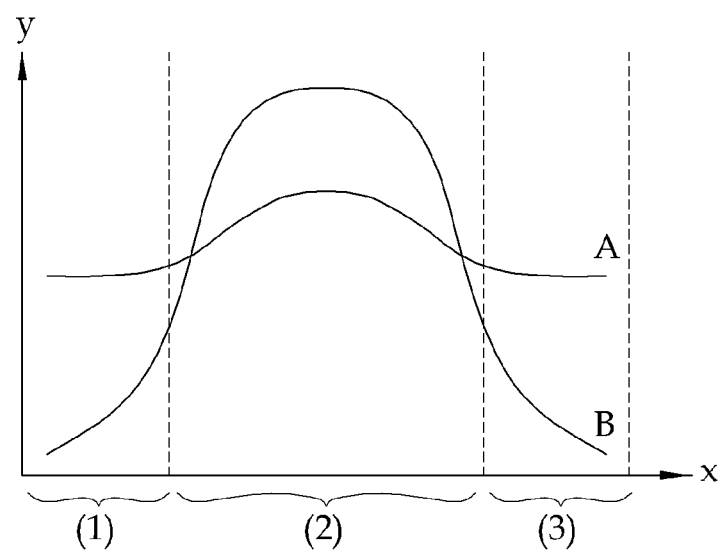
FIG. 2(c) is a graph illustrating an amount of waves reached on a waveguide and a rectenna.

FIG. 2(c) is a graph illustrating an amount of the waves which reach waveguide 110 and rectenna 120. The x-axis of the graph represents the widths of waveguide 110 and rectenna 120. Particularly, an area "(1)" indicates a width of left end portion 115 of waveguide 110, an area "(2)" indicates a width of rectenna 120 which overlaps with central portion 116 of waveguide 110, and an area "(3)" indicates a width of right end portion 117 of waveguide 110. The y-axis of the graph represents an amount of the waves. In FIG. 2(c), a curved line "A" represents the amount of the waves over areas (1) through (3) before passing through waveguide 110. As shown with curved line "A," the amount of waves in areas (1) through (3) are considerably even. In FIG. 2(c), a curved line "B" represents the amount of the waves over areas (1) through (3) after passing through waveguide 110. Most of waves, including even the waves (for example, waves 142-1 and 142-2 illustrated in FIG. 2(b)), which arrive at the portions of waveguide 110 outside the width of rectenna 120, reach rectenna 120 without scattering to the outside of the width of rectenna 120 as illustrated above with reference to FIG. 2(b). Thus, the amount of the waves within area (2) is substantially larger than the amount of the waves in areas (1) and (3), as shown with curved line "B."

If waves 142-1 to 142-5 are transmitted from external power source 140 without passing through waveguide 110, waves 142-1 and 142-2 will be scattered to the outside of the width of rectenna 120. In such a case, the electric power carried by waves 142-3 to 142-5 are used to drive electric device 130, and the electric power carried by waves 142-1 and 142-2 are wasted.

In some embodiments, the negative refractive index medium may be configured with a particular physical structure or a particular chemical composition or structure. For example, the negative refractive index medium may include a metamaterial. Here, the term "metamaterial" refers to an artificial material that has negative refractive index.

Figure 3:
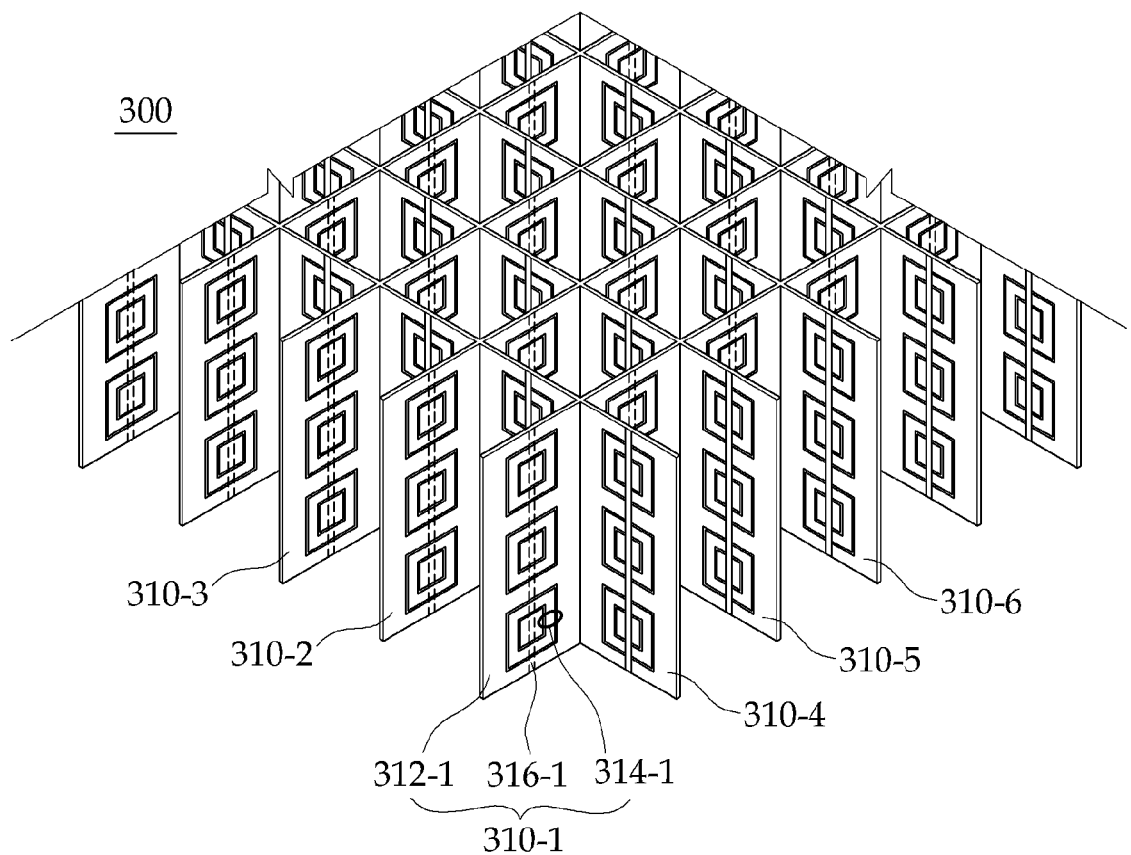
FIG. 3 is a schematic diagram of an illustrative embodiment of a metamaterial.

In one embodiment, the metamaterial may be configured with a two-dimensional array of repeated unit cells of copper strips and split ring resonators on interlocking strips of standard circuit board material. FIG. 3 is a schematic diagram of an illustrative embodiment of a metamaterial. FIG. 3 illustrates a metamaterial 300 including a multiple number of unit cells, for example, 310-1 through 310-6. Each unit cell (for example, a unit cell 310-1) has a fiber glass circuit board 312-1. On one side of fiber glass circuit board 312-1, square copper split ring resonators 314-1 are formed. On the other side of fiber glass circuit board 312-1, a copper wire strip 316-1 is formed. Although unit cell 310-1 has only three square copper split ring resonators 314-1 and one copper wire strip 316-1 for the purpose of description, it will be apparent to one of ordinary skills in the art that unit cells 310-1 may have less or more than three square copper split ring resonators and more than one copper wire strip. Unit cells 310-1 through 310-6 are interlocked to form a lattice structure, as depicted in FIG. 3. Metamaterial 300 may be fabricated by subjecting 0.25-mm thick G10 fiber glass circuit board material to shadow mask/etching, cutting the board, and assembling the board into an interlocking unit. Experimentally, metamaterial 300 exhibits negative refractive index at wavelengths of waves, for examples, about 1 mm to 20 cm, about 15 mm to 1 cm or about 27 mm to 30 mm. For more details on structures, properties, and fabrication of metamaterial 300, see R. A. Shelby, et al., "Experimental verification of a negative index of refraction," Science, Vol. 292, p. 77, published on 6 Apr. 2001, which is incorporated by reference herein in its entirety.

In another embodiment, the metamaterial may include a quantum metamaterial. The term "quantum metamaterial" refers to an artificial material fabricated to have negative refractive index by manipulating a chemical composition or a structure of a material (for example, by substituting some of atoms and/or molecules or changing an arrangement of atoms and/or molecules). For example, a quantum metamaterial can be fabricated from a silicon-based plate doped with other materials than silicon.

FIG. 4(a) is a schematic diagram of another illustrative embodiment of an apparatus including a waveguide operable with a rectenna. In FIG. 4(a), the same elements as those shown in FIG. 1(a) are denoted by the same reference numerals. Waveguide 410 may include a surface plasmon medium. As used herein, the term "surface plasmon medium" refers to a medium that exhibits a surface plasmon resonance. As used herein, the term "surface plasmon resonance" refers to a collective oscillation of electrons excited by a wave.

Waveguide 410 includes a first component 414, a second component 416, and a dielectric component 412 interposed between first and second components 414 and 416. In some embodiments, first and second components 414 and 416 may be composed of a surface plasmon material. As used herein, the term "surface plasmon material" refers to a material exhibiting a surface plasmon resonance in its interface with a dielectric material. By way of examples, the surface plasmon material may include Au, Ag, Cu, Ti, Cr or an alloy thereof, without limitation. By way of examples, dielectric component 412 may be composed of a dielectric material, such as air or silicon dioxide. First and second components 414 and 416 and dielectric component 412 configure the surface plasmon medium exhibiting the surface Plasmon resonance, as will be described later.

In some embodiments, each of first and second components 414 and 416 may have a shape of a hexahedron or a cube, and a dimension of several nanometers to several micrometers (for example, a width of about 0.5 nm to 200 mm, about 1 nm to 1 mm or about 5 nm to 100 nm, and a thickness of about 0.1 nm to 100 mm, about 1 nm to 50 mm or about 20 nm to 500 nm, without limitation). Dielectric component 412 may have a shape of a hexahedron or a cube and a dimension of several nanometers to several micrometers (for example, a width of about 0.1 nm to 100 mm, about 1 nm to 500 nm or about 3 nm to 50 nm, and a thickness of about 0.1 nm to 100 mm, about 1 nm to 50 mm or about 20 nm to 500 nm, without limitation).

In some embodiments, first component 414 may have a left end portion 415 which is on an opposite side of dielectric component 412, and second component 416 may have a right end portion 417 which is on an opposite side of dielectric component 412. Left and right end portions 415 and 417 extend out of the width of rectenna 120, respectively. Thus, left and right end portions 415 and 417 are not supported by rectenna 120, as depicted in FIG. 4(a). Each of left and right end portions 415 and 417 may have a width of several nanometers to several micrometers. For example, each of left and right end portions 415 and 117 may have a width of about 0.25 nm to 50 mm, about 1 nm to 25 mm or about 5 nm to 250 nm, without limitation.

First component 414 and second component 416 of waveguide 410 generate the surface plasmon resonance, which will be described in detail later. The surface plasmon resonance causes an electric field generated by wave 142 to be mostly distributed in dielectric component 412. The distributed electric field propagates into rectenna 120. In an embodiment where rectenna 120 optionally includes conducting elements, the electric field vibrates charges (for example, electrons and holes) in the conducting elements of rectenna 120. This vibration of charges creates alternating currents. The alternating currents are rectified by rectifying elements (for example, diodes) of rectenna 120 to generate an electric power as described above. Thus, the more electric field is distributed in dielectric component 412, the more electric power is generated.

Electrons, located at an interface 424 between dielectric component 412 and first component 414 and at an interface 426 between dielectric component 412 and second component 416, are collectively oscillated due to the surface plasmon materials of first and second components 414 and 416, and thus a density of the electrons in first and second components 414 and 416 is fluctuated. This collective oscillation of the electrons is the surface plasmon resonance as defined above. The surface plasmon resonance makes first and second components 414 and 416 to have large absolute values of permittivity. Since electric flux densities in dielectric component 412 and first and second components 414 and 416 are the same, and electric flux densities are represented as a multiplication of permittivity and an electric field intensity, the following Equation (2) can be derived.

$$\frac{D_{dielectric}}{D_{plasmon}} = \frac{\varepsilon_{dielectric} \cdot E_{dielectric}}{\varepsilon_{plasmon} \cdot E_{plasmon}} = 1 \qquad \text{Equation (2)}$$

Here, $D_{dielectric}$ and $D_{plasmon}$ respectively refer to electric flux densities of dielectric component 412 and first and second components 414 and 416 of waveguide 410. $\varepsilon_{dielectric}$ and $\varepsilon_{plasmon}$ respectively refer to permittivities of dielectric component 412 and first and second components 414 and 416 of waveguide 410. $E_{dielectric}$ and $E_{plasmon}$ respectively refer to electric field intensities of dielectric component 412 and first and second components 414 and 416 of waveguide 410. The following Equation (3) is derived from Equation (2) above.

$$\frac{E_{dielectric}}{E_{plasmon}} = \frac{\varepsilon_{plasmon}}{\varepsilon_{dielectric}} \qquad \text{Equation (3)}$$

Since permittivity $\varepsilon_{plasmon}$ of first and second components 414 and 416 is greater than permittivity $\varepsilon_{dielectric}$ of dielectric component 412 in absolute value as described above, electric field intensity $E_{dielectric}$ of dielectric component 412 is greater than electric field intensity $E_{plasmon}$ of first and second components 414 and 416. Thus, when an external electric field is applied to waveguide 410, the electric field can be mostly distributed in dielectric component 412.

Figure 4B:
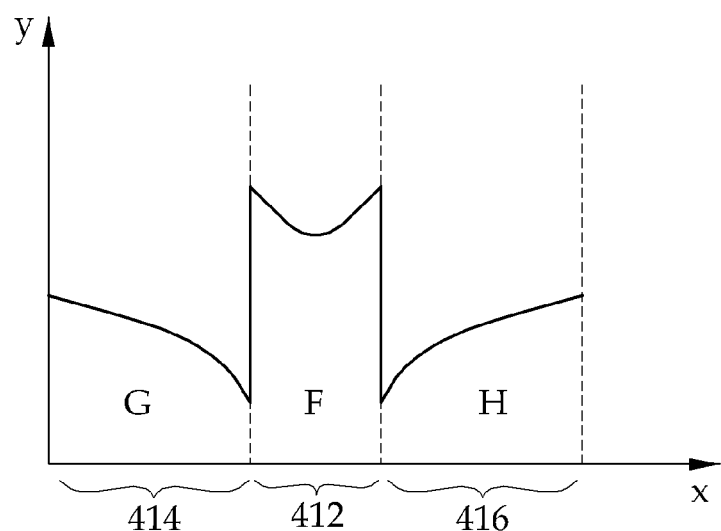
FIG. 4(b) is a graph showing a distribution of an electric field in the first component, dielectric component and second component of FIG. 4(a).

FIG. 4(b) is a graph showing a distribution of an electric field in first component 414, dielectric component 412 and second component 416, as depicted in FIG. 4(a). The y-axis of the graph represents the amounts of the electric field distributed in first component 414, dielectric component 412 and second component 416. The x-axis of the graph represents the cross-sections of first component 414, dielectric component 412 and second component 416 as depicted in FIG. 4(a). A region "F" indicates the amount of the electric field distributed in dielectric component 412. A region "G" indicates the amount of the electric field distributed in first component 414. A region "H" indicates the amount of the electric field distributed in second component 416. As described above, when an electric field is applied from an external source (for example, external power source 140), the applied electric field is concentrated within dielectric component 412 due to the permittivity difference between dielectric component 412 and first and second components 414 and 416.

Referring back to FIG. 4(a), external power source 140 transmits wave 142 carrying an electric power to drive electric device 130. Since each of first and second components 414 and 416 includes the surface plasmon material and dielectric component 412 includes the dielectric material, the permittivity of first and second components 414 and 416 are greater than the permittivity of dielectric component 412. Thus, when wave 142 is received at waveguide 410 including first and second components 414 and 416 and dielectric component 412, the electric field from wave 142 is mostly distributed in dielectric component 412 due to the permittivity difference, as described above. The electric field distributed in dielectric component 412 propagates to rectenna 120 which is located under dielectric component 412. Because the permittivity difference can makes the electric field concentrated into dielectric component 412, the electric power from wave 142 is not wasted although wave 142 reach left and right end portions 415 and 417 which extend out of the width of rectenna 120. Rectenna 120 receives the electric field propagating from waveguide 410 and generates an electric power as described above.

Figure 5:
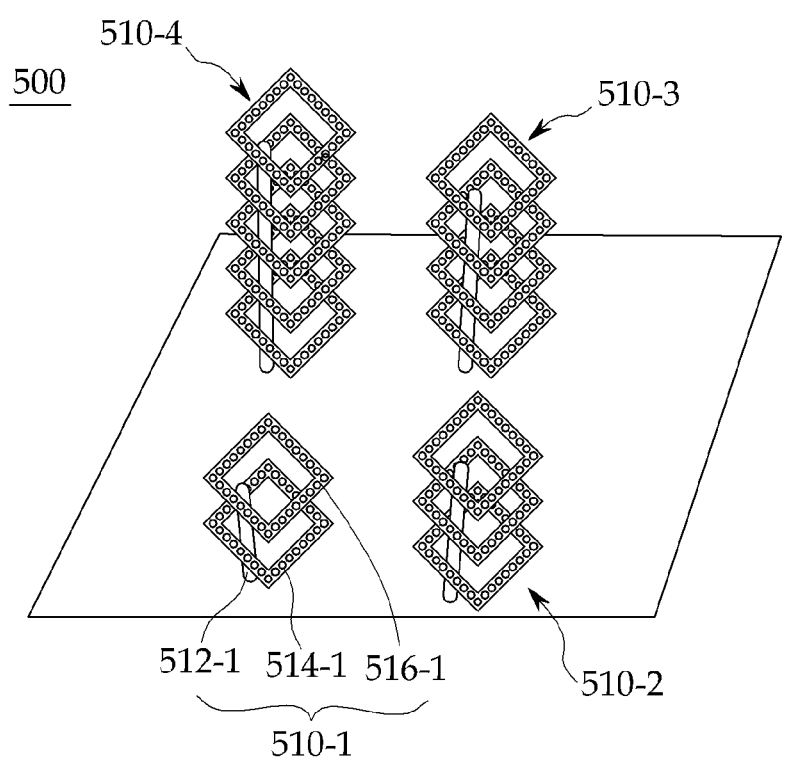
FIG. 5 is a schematic diagram of an illustrative embodiment of a loop-wire medium.

In another embodiment, the surface plasmon medium may have a loop-wire structure which exhibits the surface plasmon resonance. This loop-wire structure is configured with an artificial structure to generate the surface plasmon resonance. FIG. 5 is a schematic diagram of an illustrative embodiment of a loop-wire medium. A loop-wire structure 500 includes a multiple number of wire elements 510-1 through 510-4. A wire element 510-1 includes a vertical wire 512-1 with planar loops 514-1 and 516-1 wound at intervals. Although loop-wire structure 500 has four wire elements 510-1 through 510-4 for the purpose of description, it will be apparent to one of ordinary skills in the art that loop-wire structure 500 may have more or less than four wire elements. Also, although wire element 510-1 has two planar loops 514-1 and 516-1 for the purpose of description, it will be apparent to one of ordinary skills in the art that wire element 510-1 may have more or less than two planar loops. Experimentally, loop-wire structure 500 exhibits the surface plasmon resonance at wavelengths of waves for example, about 1 mm to 25 cm, 20 mm to 10 cm or about 37.5 mm to 60 mm. For more details on structures, properties and fabrication of loop-wire structure 500, see D. R. Smith et al., "Loop-wire medium for investigating plasmons at wave frequencies," Applied Physics Letters, Vol. 75, No. 10, p. 1425, published on 6 Sep. 1999, which is incorporated by reference herein in its entirety.

FIG. 6 is a schematic diagram of still another embodiment of an apparatus including a waveguide operable with a rectenna. In FIG. 6, the same elements as those shown in FIG. 1(a) are denoted by the same reference numerals. A waveguide 610 is different from waveguide 110 of FIG. 1(a) in that waveguide 610 includes three components, for example, a first component 612, a second component 614 and a third component 616. First, second and third components 612, 614 and 616 are spaced from each other, and the spaces therebetween may be filled with dielectric materials, such as air. In one embodiment, each of first, second and third components 612, 614 and 616 may include the negative refractive medium as described above. In another embodiment, each of first, second and third components 612, 614 and 616 may include the surface plasmon material as described above. The shape, width and thickness of first, second and third components 612, 614 and 616 are substantially the same as the shape, width and thickness described above for first and second components 414 and 416.

FIG. 7 is a schematic diagram of still another embodiment of an apparatus including a waveguide operable with a rectenna. In FIG. 7, the same elements as those shown in FIG. 1(a) are denoted by the same reference numerals. A waveguide 710 includes the surface plasmon material to refract a wave into a width of a rectenna, as illustrated in FIG. 4. However, waveguide 710 includes first and second components 714 and 716 spaced from each other, while waveguide 410 of FIG. 4(a) includes first and second components 414 and 416 and dielectric component 412 interposed therebetween. Rectenna 720 includes an antenna part 722 and a rectifier part 724. Rectifier part 724 is an elongated substrate and antenna part 722 is protruded from a part of rectifier part 724. A width of antenna part 722 is substantially identical to a distance between first and second components 714 and 716. Thus, rectenna 720 may be located under waveguide 710 such that antenna part 722 is located between first and second components 714 and 716.

Antenna part 722 may include a dielectric material, such as silicon dioxide. Each of first and second components 714 and 716 may include the surface plasmon material as described above. An electric field may be mostly distributed in antenna part 722 of rectenna 720 because antenna part 722, including the dielectric material, has smaller permittivity than the permittivity of first and second components 714 and 716, as described above. Although waveguide 710 has two components (first and second components 714 and 716) and rectenna 720 has only one protruding part (antenna part 722) for the purpose of description, a waveguide and a rectenna according to another embodiment may have more than two components and more than one protruding part, respectively. By way of example, a waveguide having four components spaced from each other may be placed on a rectenna having three protruding parts such that each protruding part of the rectenna is interposed between two components of the waveguide.

The shape, material, structure, width and thickness of first and second components 714 and 716 are substantially the same as the shape, material, structure, width and thickness of first and second components 414 and 416 of FIG. 4(a). The shape, width and thickness of antenna part 722 are substantially the same as the shape, width and thickness described above for dielectric component 412 of FIG. 4(a). The shape, width and thickness of rectifier part 724 are substantially the same as the shape, width and thickness described above for rectenna 120 of FIG. 1(a).

In other embodiments, a waveguide may include both the negative refractive index medium and the surface plasmon medium. For example, referring back to FIG. 4(a), one (for example, first component 414) of first and second components 414 and 416 may include the negative refractive index medium, and the other one (for example, second component 416) and dielectric component 412 may configure the surface plasmon medium. For another example, referring back to FIG. 6, two (for example, first and second components 612 and 614) of first, second and third components 612, 614 and 616 may include the negative refractive index medium, and the other one (for example, third component 616) and a space between second and third components 614 and 616 may configure the surface plasmon medium. In these examples, the waves, transmitted from an external power source, can be guided to reach within the width of the rectenna by both a negative refraction and a surface plasmon resonance.

Figure 8A:
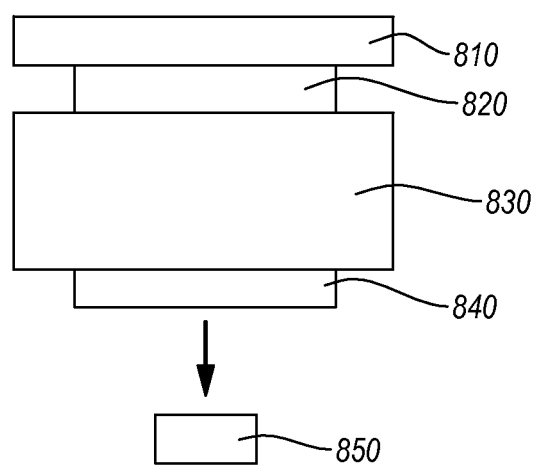
FIG. 8(a) is a schematic diagram of an illustrative embodiment of a health monitoring system.

In some embodiments, waveguide 110, 410, 610 or 710 may be included in a health monitoring system. The term "health monitoring system" refers to a system with which health status of a creature (for example, a human being) may be monitored. FIG. 8(a) is a schematic diagram of an illustrative embodiment of a health monitoring system. A health monitoring system 800 includes a waveguide 810, a rectenna 820, a detection device 830 and a transmitter 840. Waveguide 810 may receive a wave transmitted from an external power source (not shown) and guide the wave to reach within a width of rectenna 820. The constitution, dimension and material for waveguide 810 are substantially the same as the constitution, dimension and material described above for waveguide 110. Although FIG. 8(a) illustrates waveguide 810 has the same configuration as that of waveguide 110, it will be apparent to those skilled in the art that waveguide 810 may have the same constitution, dimension and material described for waveguide 410, 610 or 710. Rectenna 820 may be positioned under waveguide 810, and receive and rectify the waves guided by waveguide 810 to generate an electric power to drive detection device 830. The constitution and dimension for rectenna 820 are substantially the same as the configuration and dimension described above for rectenna 120 or 720.

Detection device 830 detects a health status of a creature and generates an electric signal (for example, a voltage signal or a current signal). In some embodiments where health monitoring system 800 are placed on a body of a creature (for example, a body of a human) or introduced inside the body of the creature, detection device 830 may detect a physiological or chemical change in or on the body of the creature and generate an electric signal representing the detected changes in the body of the creature. The health status can be illustrated with electronic features of the electric signal, such as a magnitude, wave form or frequency, without limitation. For example, a high frequency of an electric signal can represent a high heart rate. Transmitter 840 transmits the electric signal to an external device 850, such as an external monitor. The external monitor, for example, a heart rate monitor, displays a change of a frequency of the electric signal.

Figure 8B:
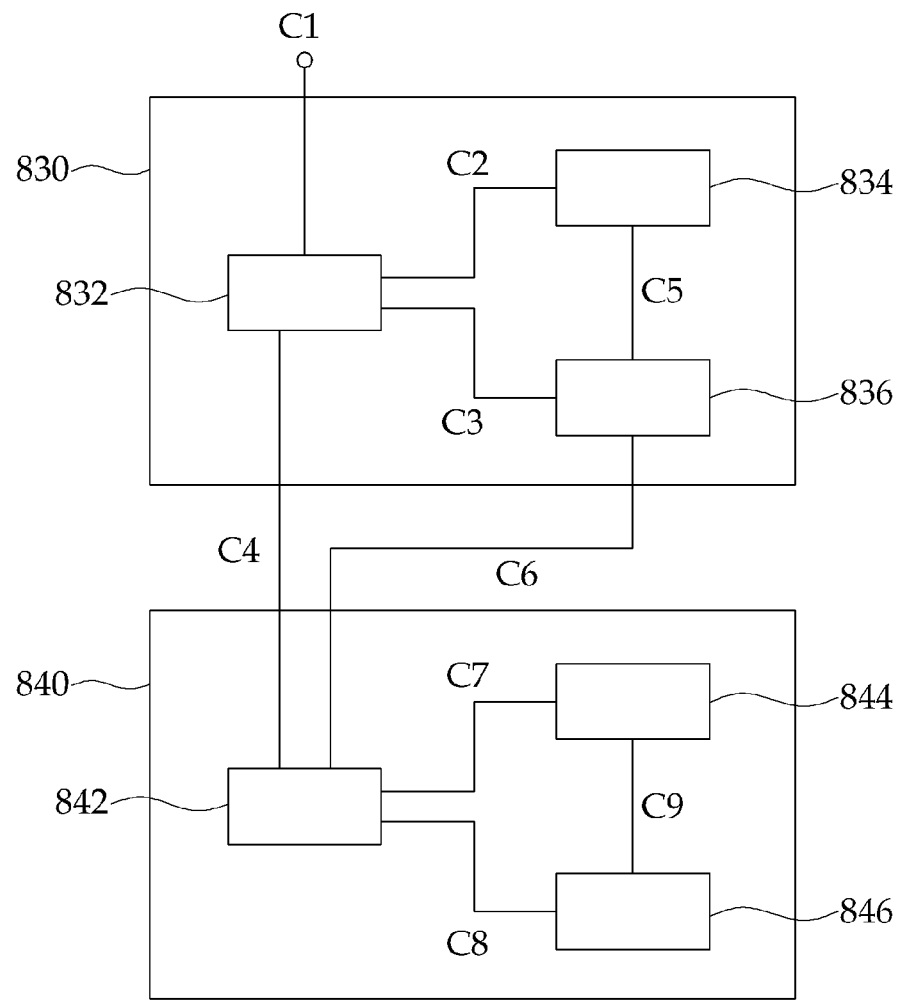
FIG. 8(b) is a block diagram of an illustrative embodiment of the detection device and transmitter of FIG. 8(a).

Constitutions and operations of detection device 830 and transmitter 840 will be described hereinafter with reference to FIG. 8(*b*). FIG. 8(*b*) is a block diagram of an illustrative embodiment of detection device 830 and transmitter 840. In this embodiment, detection device 830 includes a power manager 832, a sensing part 834 and an interface 836. Transmitter 840 includes a controller 842, an encoder 844 and an antenna 846. Power manager 832 is electrically connected to rectenna 820 via a connection C1. Connection C1 may be a wired or wireless connection. Power manager 832 receives the electric power from rectenna 820 via connection C1. Power manager 832 is electrically connected to sensing part 834, interface 836 and controller 842 via connections C2, C3 and C4 to supply an electric power to sensing part 834, interface 836 and controller 842, respectively. Each of connections C2, C3 and C4 may be a wired or wireless connection. Power manager 832 may have a control unit (not shown) to manage the reception of the electric power from rectenna 820 and the supply of the electric power to sensing part 834, interface 836 and controller 842. For example, the control unit may be implemented with a microprocessor.

Sensing part 834 detects a health status of a creature and generates an electric signal (such as a voltage signal or a current signal). As described above, the electric signal can represent the health status, for example, by a magnitude, waveform or frequency of the electric signal. The health status may include an existence/concentration of a particular chemical in the body of a creature, and a blood pressure, a heart rate or a body temperature of the creature, without limitation. In other embodiment, sensing part 834 may include at least one of a biosensor (not shown) and a chemosensor (not shown). The biosensor detects a health status regarding a physiological change or process. The biosensor may include a glucose sensor, an airborne bacteria sensor and a drug residue sensor, without limitation. The chemosensor is a sensory receptor that detects certain chemical stimuli in the environment. The chemosensor may include a breathing rate sensor and a heart rate sensor, without limitation.

Interface 836 is connected with sensing part 834 via a connection C5 to receive the electric signal generated by sensing part 834. Interface 836 is connected to controller 842 of transmitter 840 via a connection C6 to provide a signal communication between detection device 830 and transmitter 840. For example, interface 836 provides controller 842 of transmitter 840 with the electric signal received from sensing part 834 of detection device 830. Each of connections C5 and C6 may be a wired or wireless connection.

Controller 842 is provided with an electric power from power manager 832 via connection C4 and an electric signal from interface 836 via connection C6. Controller 842 supplies the electric power to encoder 844 and antenna 846 via connections C7 and C8, respectively. Controller 842 provides encoder 844 with the electric signal provided by interface 836 via connection C7. Upon receipt of the electric signal, encoder 844 encodes the electric signal using a well-known encoding scheme, such as Manchester coding and differential binary phase shift keying coding, without limitation. Encoder 844 outputs the encoded electric signal to antenna 846 via a connection C9. Then, transmitter 840 transmits the encoded electric signal including the detected health status through antenna 846. Each of connections C7, C8 and C9 may be a wired or wireless connection. Although detection device 830 and transmitter 840 are illustrated with reference to FIG. 8(*b*) for description, it will be apparent to one of skill in the art that other configurations are also applicable as long as the configurations can be operable with waveguide 110, 410, 610 or 710.

In one embodiment, health monitoring system 800 may be formed and sized to be introduced into a body of a creature. For example, health monitoring system 800 may be included in a capsule. The capsule may dissolve in the body of the creature and release health monitoring system 800 into the body. In this embodiment, detection device 830 of health monitoring system 800 may further include at least one location signal generator (not shown). The location signal generator identifies a current location of health monitoring system 800 in the body of the creature and generates a signal representing the identified current location.

In another embodiment, health monitoring system 800 may be formed and sized to be attached on an outer surface of a creature. For example, health monitoring system 800 may be attached to an elastic band such that the creature can wear on its arm, body or leg. In this embodiment, health monitoring system 800 may have a size of several micrometers to several millimeters, for example, about 1 μm to 500 mm, about 100 μm to 100 mm or about 1 mm to 50 mm.

In other embodiments, waveguide 110, 410, 610 or 710 may be used in a ubiquitous environment. The term "ubiquitous environment" refers to an environment where a user may access to a computer network regardless of the user's location. The ubiquitous environment may include ubiquitous banking system, ubiquitous nursing system and ubiquitous learning system. In the ubiquitous environment, a user can use waveguide 110, 410, 610 or 710 with a wireless device which does not have an internal power source. By using waveguide 110, 410, 610 or 710, the user can efficiently receive the electric power transmitted from an external power source.

Figure 9:
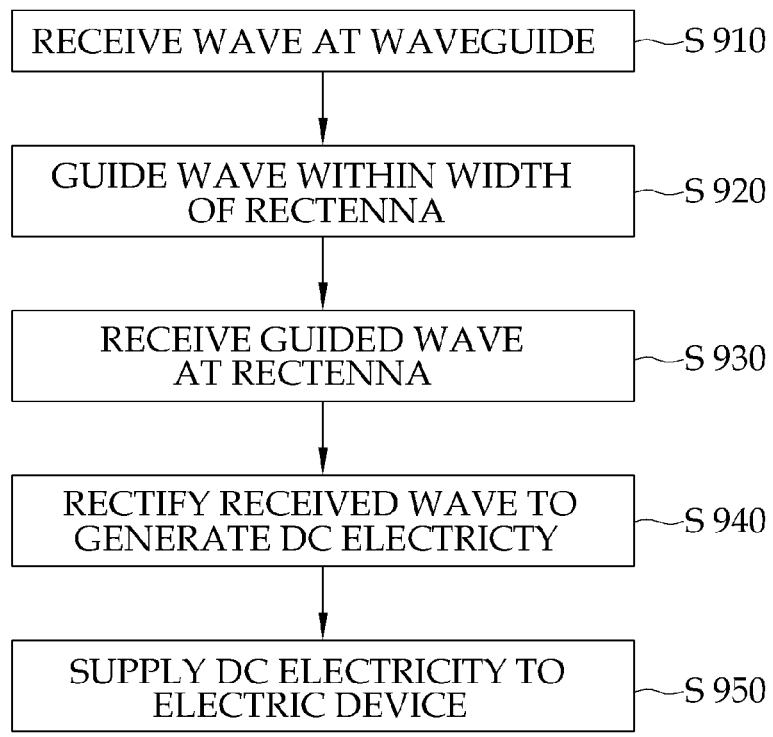
FIG. 9 is a flow chart illustrating an illustrative embodiment of a method of supplying an electric power to an electric device.

A method of supplying an electric power to an electric device will be described with reference to FIGS. 1, 4(*a*) and 9. FIG. 9 is a flow chart illustrating an illustrative embodiment of the method. Wave 142 is transmitted from an external power source 140 and received at waveguide 110 or 410 (S 910). At waveguide 110 or 410, wave 142 is guided to reach within a width of rectenna 120 (S 920). In an embodiment where waveguide 110 includes the negative refraction index medium, wave 142 is guided to refract within the width of rectenna 120 at the negative refraction index medium of waveguide 110. In another embodiment where waveguide 410 includes the surface plasmon medium, wave 142 is guided to be concentrated within the width of rectenna 120 by the surface plasmon resonance of the surface plasmon medium. Then, the guided wave is received at rectenna 120 (S 930). The received wave is rectified at rectenna 120 to generate a DC electricity (S 940). The generated DC electricity is supplied to electric device 130 (S 950). Since waveguide 110 or 410 guides wave 142 from external power source 140 to reach within a width of rectenna 120 by the negative refraction or the surface plasmon resonance, an electric power carried on wave 142 can efficiently be transmitted to electric device 130.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A health monitoring system comprising:
   a detection device configured to detect a health status of a creature;
   a rectenna;
   a waveguide configured to receive a wave transmitted from an external power source and to guide the wave to reach within a width of the rectenna, the waveguide having a width greater than the width of the rectenna, the external power source positioned on a first side of the waveguide;

wherein portions of the wave in the waveguide that are outside of the width of the rectenna are guided to reach the rectenna, wherein the rectenna is positioned on a second side of the waveguide and configured to receive and to rectify the guided wave to generate an electric power to drive the detection device; and a transmitter configured to transmit the detected health status to an external device.

2. The health monitoring system of claim 1, wherein the detection device comprises at least one of a chemosensor and a biosensor to sense the health status.

3. The health monitoring system of claim 1, wherein the health monitoring system is configured to be inserted into a body of the creature or configured to be attached on an outer surface of the creature.

4. The health monitoring system of claim 1, wherein the external device comprises a monitor to display the detected health status.

5. The health monitoring system of claim 1, wherein the waveguide includes a negative refractive index medium to refract the wave to reach the width of the rectenna.

6. The health monitoring system of claim 5, wherein the negative refractive index medium comprises a metamaterial.

7. The health monitoring system of claim 6, wherein the metamaterial comprises a two-dimensional array of repeated unit cells of copper strips and split ring resonators on interlocking strips of standard circuit board material.

8. The health monitoring system of claim 6, wherein the metamaterial comprises a quantum metamaterial having a manipulated chemical composition and/or a structure of a material.

9. The health monitoring system of claim 1, wherein the waveguide comprises a surface plasmon medium to generate a surface plasmon resonance.

10. The health monitoring system of claim 9, wherein the surface plasmon medium comprises two or more components and one or more dielectric components interposed between the two or more components, wherein each of the two or more components is composed of a surface plasmon material and each of the one or more dielectric components is composed of a dielectric material, and wherein a permittivity of the two or more components is greater than a permittivity of the one or more dielectric components.

11. The health monitoring system of claim 9, wherein the surface plasmon medium comprises a loop-wire structure, the loop-wire structure comprises a plurality of wire elements, and each wire element comprises at least one vertical wire with at least one planar loop wound at intervals.

12. The health monitoring system of claim 9, wherein the surface plasmon medium comprises at least two components being spaced from one another, each component being composed of a surface plasmon material, and wherein the rectenna comprises a rectifier part positioned under the waveguide and at least one antenna part protruding from a part of the rectifier part such that the antenna part is located between the at least two components, and wherein the at least one antenna part is composed of a dielectric material.

13. The health monitoring system of claim 1, wherein the waveguide comprises both a negative refractive index medium to refract the wave and a surface plasmon medium to generate a surface plasmon resonance.

14. The health monitoring system of claim 1, wherein the rectenna is positioned adjacent to the waveguide.

15. The health monitoring system of claim 14, wherein the width of the rectenna is about 0.5 nm to 300 mm.

16. A health monitoring system comprising:

a detection device configured to detect a health status of a creature and that operates on electric power;

a rectenna having a width, the rectenna including an antenna part and a rectifier part;

a waveguide located between an external power source and the rectenna, the waveguide configured to receive waves transmitted from the external power source and to guide the waves to the rectenna, the waves including at least some waves outside the width of the rectenna, wherein the waveguide is configured to refract at least some waves outside the width of the rectenna such that the waves outside the width of the rectenna are received by the rectenna, wherein the rectenna is configured to receive and rectify the guided waves to generate the electric power to drive the detection device, wherein the waveguide is wirelessly coupled to the antenna part of the rectenna; and a transmitter configured to transmit the health status detected by the detection device to an external device.

17. The health monitoring system of claim 16, wherein the waveguide has a width greater than the width of the rectenna, wherein the waveguide includes a negative refractive index medium to refract the waves to reach the width of the rectenna.

18. The health monitoring system of claim 17, wherein the negative refractive index medium comprises a metamaterial.

19. The health monitoring system of claim 16, wherein the waveguide comprises a surface plasmon medium to generate a surface plasmon resonance.

20. A method for detecting a health status of a creature, the method comprising:

receiving waves from an external power source at a waveguide, the external power source positioned on a first side of the waveguide;

guiding the waves to reach within a width of a rectenna with the waveguide, wherein the rectenna is positioned on a second side of the waveguide and wherein at least some of the guided waves received at the waveguide are outside of a width of the rectenna;

rectifying the waves guided to the rectenna to generate electric power;

supplying the electric power to a detection device configured to detect the health status of the creature, wherein the electric power powers the detection device; and transmitting the health status to an external device.

21. The method of claim 20, wherein the waveguide comprises a negative refractive index medium to guide the waves including the waves outside of the width of the rectenna to the rectenna.

22. The method of claim 20, wherein the waveguide comprises a surface plasmon medium to generate a surface plasmon resonance to guide the waves to the rectenna.

* * * * *